US012678522B2

(12) United States Patent

Levy et al.

(10) Patent No.: US 12,678,522 B2

(45) Date of Patent: Jul. 14, 2026

(54) CASE FOR SANITIZING AND TRANSPORTING PRODUCTS

(71) Applicants: Darren Levy, North Fort Myers, FL (US); Frank Levy, Fort Myers, FL (US)

(72) Inventors: Darren Levy, North Fort Myers, FL (US); Frank Levy, Fort Myers, FL (US)

( * ) Notice: Subject to any disclaimer, the term of this patent is extended or adjusted under 35 U.S.C. 154(b) by 519 days.

(21) Appl. No.: 16/881,407

(22) Filed: May 22, 2020

(65) Prior Publication Data

US 2020/0368380 A1 Nov. 26, 2020

Related U.S. Application Data

(60) Provisional application No. 62/851,255, filed on May 22, 2019.

(51) Int. Cl.
*A61L 2/10* (2026.01)
*B65D 81/18* (2006.01)

(52) U.S. Cl.
CPC ................. *A61L 2/10* (2013.01); *B65D 81/18* (2013.01); *A61L 2202/122* (2013.01); *A61L 2202/16* (2013.01)

(58) Field of Classification Search
CPC ............................................... A61L 2202/122
See application file for complete search history.

(56) References Cited

U.S. PATENT DOCUMENTS

| | | | |
|---|---|---|---|
| 4,135,269 A | 1/1979 | Marston | |
| 4,301,372 A | 11/1981 | Giering et al. | |
| 5,160,699 A | 11/1992 | Siegal | |
| 6,039,928 A | 3/2000 | Roberts | |
| 6,096,264 A | 8/2000 | Peifer | |
| 6,461,568 B1 | 10/2002 | Eckhardt | |
| 6,821,355 B1 | 11/2004 | Taylor et al. | |
| 8,158,961 B2 | 4/2012 | Merkle | |
| 8,481,970 B2 | 7/2013 | Cooper | |
| 8,964,405 B2 | 2/2015 | La Porte et al. | |
| 9,339,105 B2 | 5/2016 | Levy et al. | |
| 9,339,576 B2 | 5/2016 | LaPorte et al. | |
| 9,744,254 B2 | 8/2017 | Levy et al. | |
| 9,987,384 B2 | 6/2018 | Levy et al. | |
| 2003/0034459 A1 | 2/2003 | Bonin | |

(Continued)

FOREIGN PATENT DOCUMENTS

| | | | |
|---|---|---|---|
| CN | 2879757 Y | 3/2007 | |
| CN | 102759810 A | 10/2012 | |

(Continued)

OTHER PUBLICATIONS

Translation of JP 3037304 B2, 2000.*

*Primary Examiner* — Kevin Joyner

*Assistant Examiner* — Changru Chen

(74) *Attorney, Agent, or Firm* — Welsh Flaxman & Gitler LLC

(57) ABSTRACT

A storage and sanitizing case includes a cover and a base, the cover being connected to the base for pivotal movement relative thereto. A base tray is positioned within the base for supporting products within the case. The base tray comprises a UV permeable material. The storage and sanitizing case also includes an electronic circuit board and ultraviolet lights.

3 Claims, 16 Drawing Sheets

(56) References Cited

U.S. PATENT DOCUMENTS

| | | | |
|---|---|---|---|
| 2006/0175554 | A1 | 8/2006 | Riddell |
| 2013/0063922 | A1* | 3/2013 | La Porte .................. A61L 2/10 |
| | | | 250/455.11 |
| 2018/0243454 | A1 | 8/2018 | Levy et al. |
| 2018/0256766 | A1* | 9/2018 | Gareiss ..................... F16B 2/22 |
| 2018/0357385 | A1* | 12/2018 | LaPorte ................... A61L 2/08 |

FOREIGN PATENT DOCUMENTS

| | | | | |
|---|---|---|---|---|
| JP | 3037304 | B2 * | 4/2000 | .............. A47L 7/04 |
| WO | 2008155793 | A2 | 12/2008 | |

* cited by examiner

CASE FOR SANITIZING AND TRANSPORTING PRODUCTS

CROSS REFERENCE TO RELATED APPLICATION

This application claims the benefit of U.S. Provisional Application Ser. No. 62/851,255, entitled "CASE FOR SANITIZING AND TRANSPORTING PRODUCTS," filed May 22, 2019, which is incorporated herein by reference.

BACKGROUND OF THE INVENTION

1. Field of the Invention

The present invention relates generally to a case allowing for transport and sanitizing of products in a convenient and reliable manner.

2. Description of the Related Art

Sanitizing various household objects is problematic and difficult to achieve in a convenient manner. While the need to sanitize various objects has been with us for some time, the problems associated undesirable biological agents has become even more of an issue with the recent COVID-19 pandemic as people attempt to prevent the transmission of the virus. The present invention provides a sanitizing apparatus addressing these needs.

SUMMARY

In a first aspect the storage and sanitizing case includes a cover and a base, the cover being connected to the base for pivotal movement relative thereto. A base tray is positioned within the base for supporting products within the case, the base tray comprising a UV permeable material. The storage and sanitizing case also includes an electronic circuit board and ultraviolet lights.

In some embodiments portions of the base tray are covered in a UV reflective material.

In some embodiments the UV reflective material is a metal sheet of aluminum or aluminum base alloy.

In some embodiments a cover tray is provided within the cover, wherein the cover tray and base tray align when the case is closed so as to define a cavity in which a product is retained.

In some embodiments the cover tray comprises of a UV permeable material.

In some embodiments portions of the base tray and cover tray are covered in a UV reflective material.

In some embodiments the ultraviolet lights include two ultraviolet lights secured along an interior surface of the base, between the base and a base tray, in alignment with a side wall of the base.

In some embodiments two ultraviolet lights are secured along an interior surface of the cover along a cover wall in alignment with a side wall of the cover.

In some embodiments an actuator transmits a signal to the circuit board when the cover is closed upon the base causing power to be applied to the ultraviolet lights.

In some embodiments the ultraviolet lights are centrally mounted so as to extend upwardly from the base.

In some embodiments a plurality of product gripping supports are provided, each of the plurality of product gripping supports includes a support base and first and second support arms extending upwardly and to which first and second bracket arms are pivotally secured, wherein a space between the first and second bracket arms defines a product recess. Centers of the first and second bracket arms are pivotally secured to the first and second support arms and a securing band extends therebetween.

In some embodiments the plurality of product gripping supports comprise quartz.

In some embodiment the securing band is made of a UV permeable resilient material.

In another aspect the storage and sanitizing case includes a cover and a base, the cover being connected to the base for pivotal movement relative thereto. The storage and sanitizing case also includes an electronic circuit board and ultraviolet lights. A plurality of product gripping supports are provided. Each of the plurality of product gripping supports includes a support base and first and second support arms extending upwardly and to which first and second bracket arms are pivotally secured. A space between the first and second bracket arms defines a product recess and centers of the first and second bracket arms are pivotally secured to the first and second support arms and a securing band extends therebetween.

In yet another aspect the storage and sanitizing case includes a telescopically expandable housing including a first end and second end. The housing includes a first end member and a second end member that telescopically moves relative to the first end member between a storage configuration and a use configuration. The storage and sanitizing case also includes an electronic circuit board and ultraviolet lights positioned within the telescopically expandable housing.

In some embodiments the first end member includes a base member and plurality of side walls extending therefrom.

In some embodiments the second end member includes a door assembly and a plurality of side walls extending therefrom.

In some embodiments portions of the telescopically expandable housing are covered in a UV reflective material.

In some embodiments the ultraviolet lights are positioned between the first end member and an interior tray.

Other advantages of the present invention will become apparent from the following detailed description when viewed in conjunction with the accompanying drawings, which set forth certain embodiments of the invention.

DESCRIPTION OF THE PREFERRED EMBODIMENTS

Figure 1:
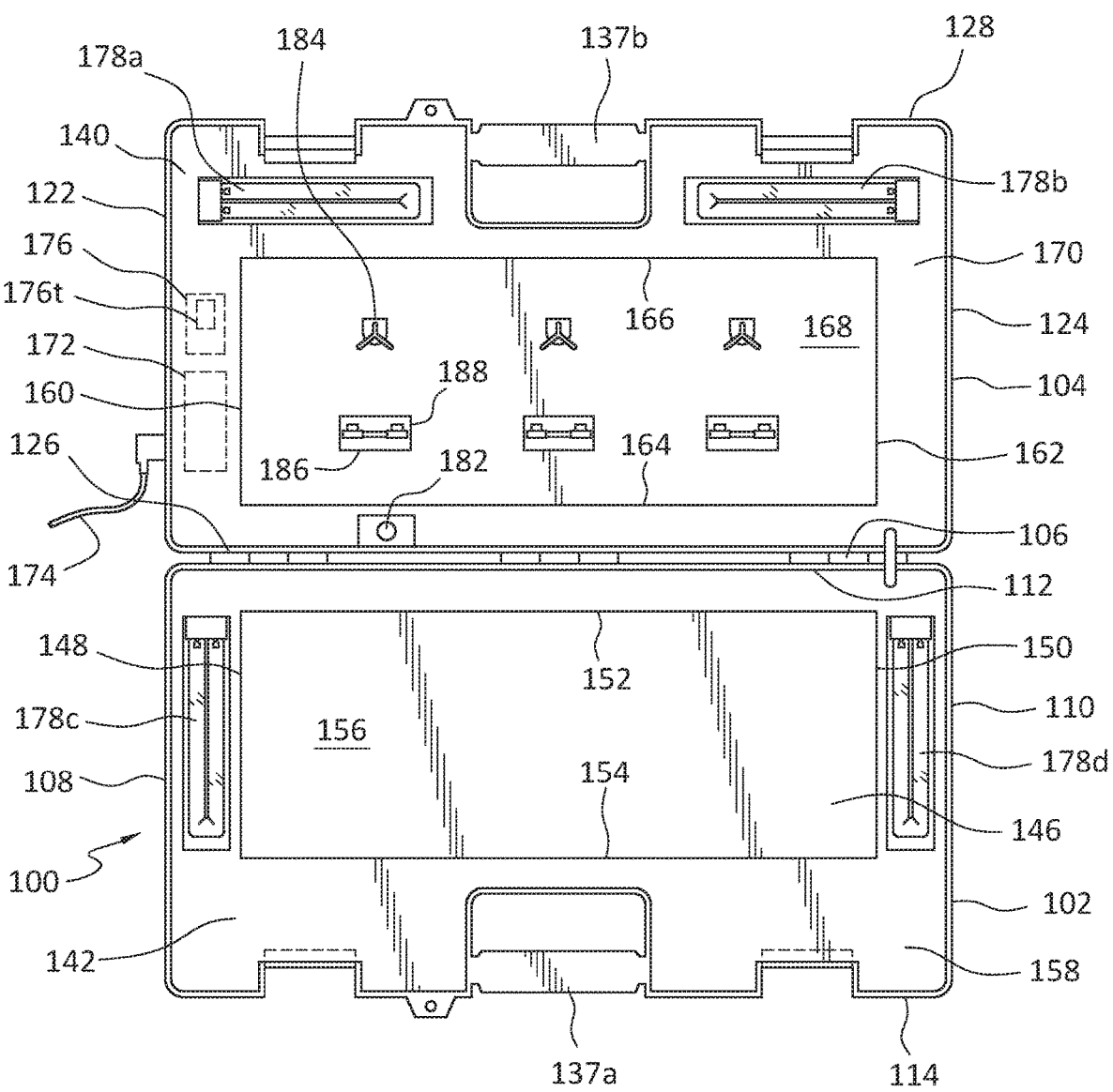
FIG. 1 is a top plan view of the present storage and sanitizing case in an open configuration.
Figure 2:
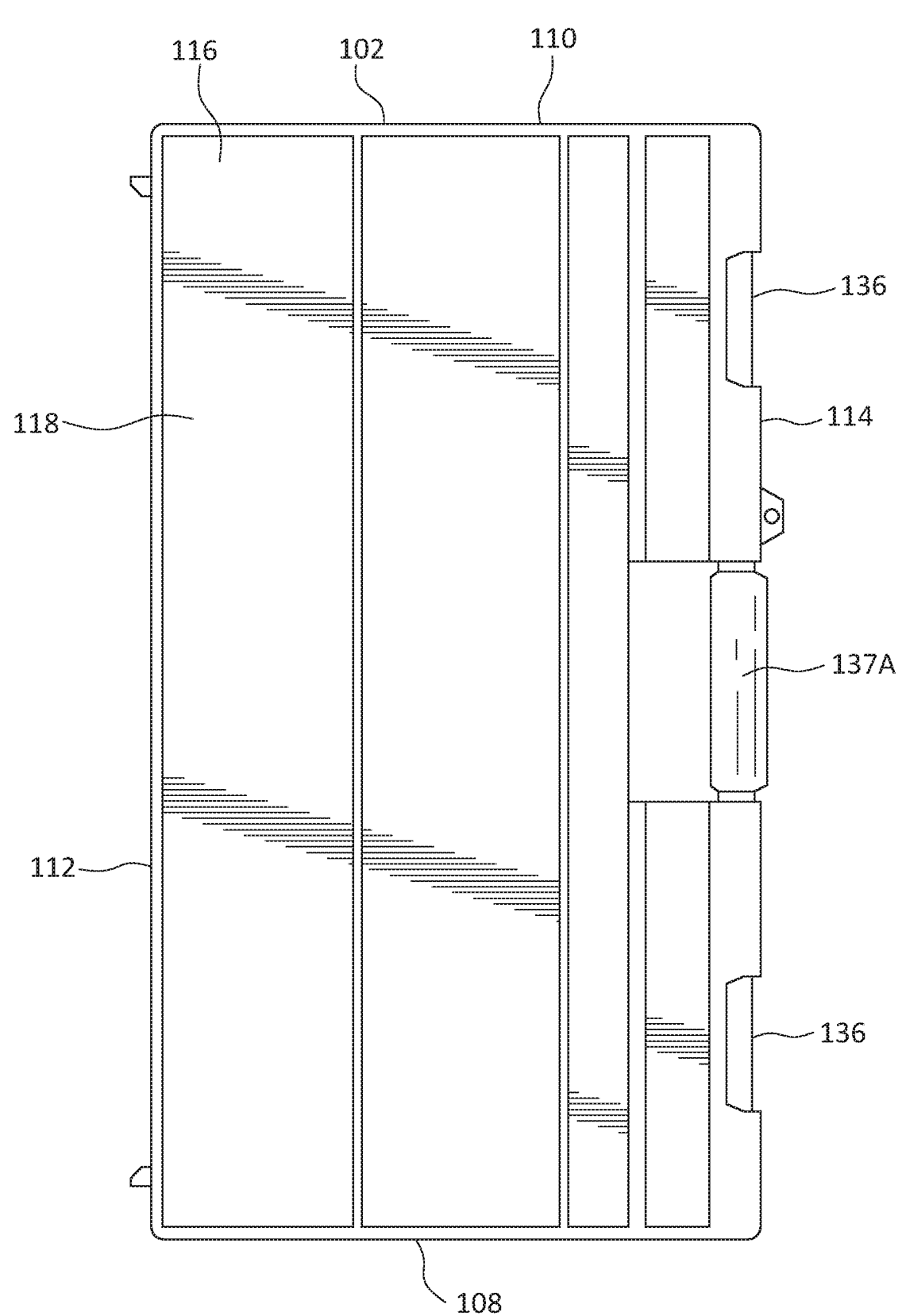
FIG. 2 is a top plan view of the present storage and sanitizing case in a closed configuration.
Figure 3:
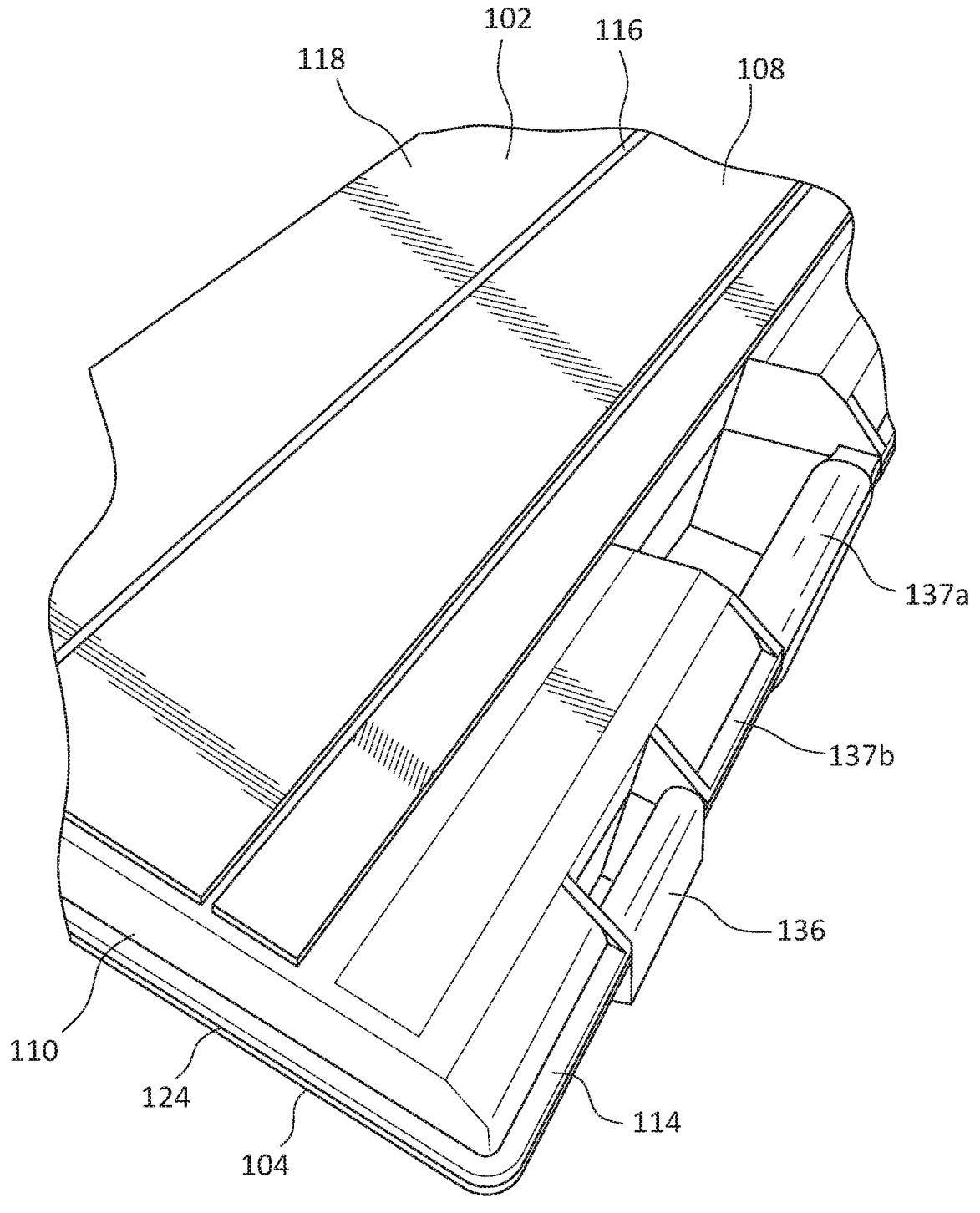
FIG. 3 is a top perspective view of the present storage and sanitizing case in a closed configuration.
Figure 4:
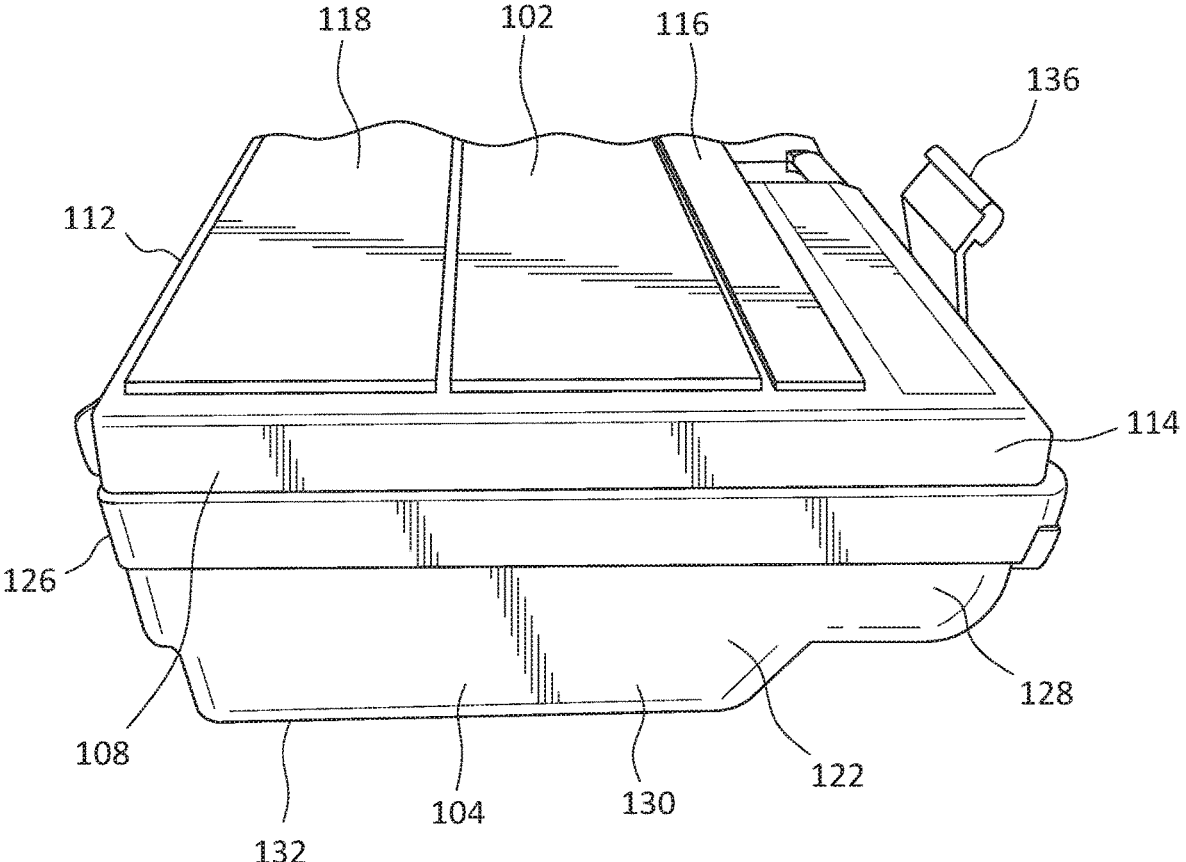
FIG. 4 is a side elevation view of the present storage and sanitizing case in a closed configuration.
Figure 5:
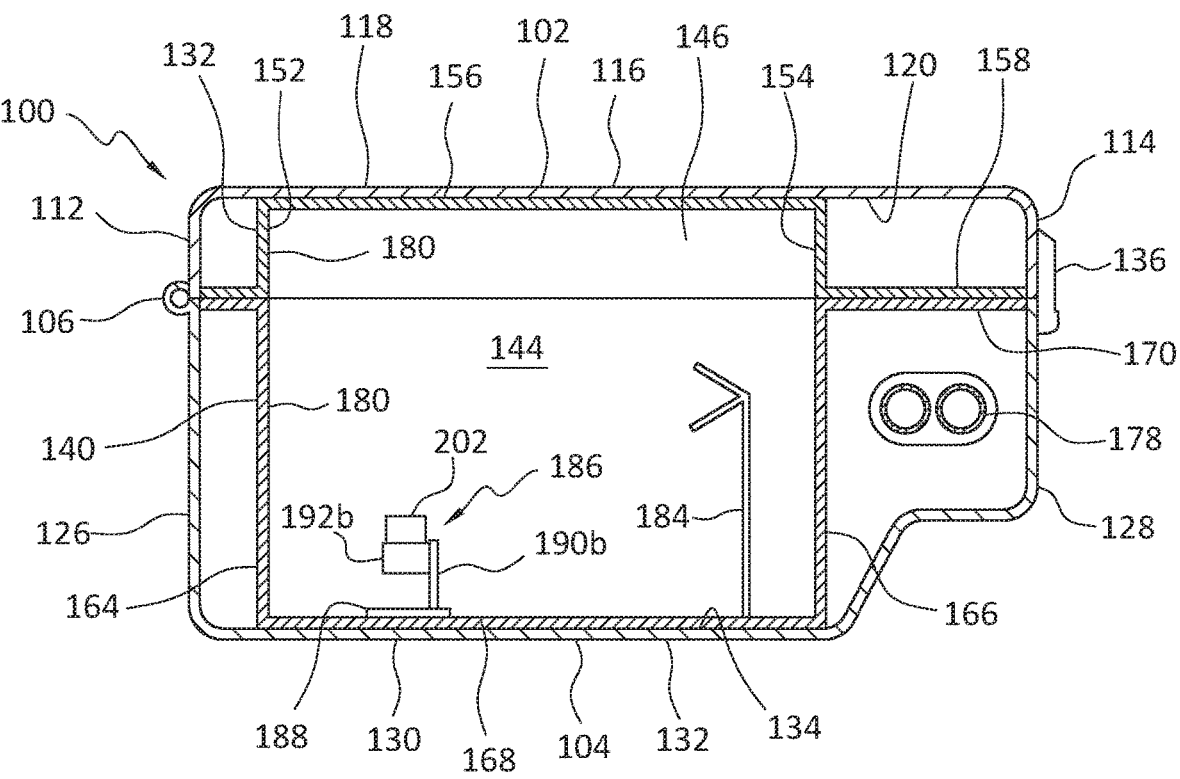
FIG. 5 is a cross sectional view of the present storage and sanitizing case in a closed configuration.
Figure 5A:
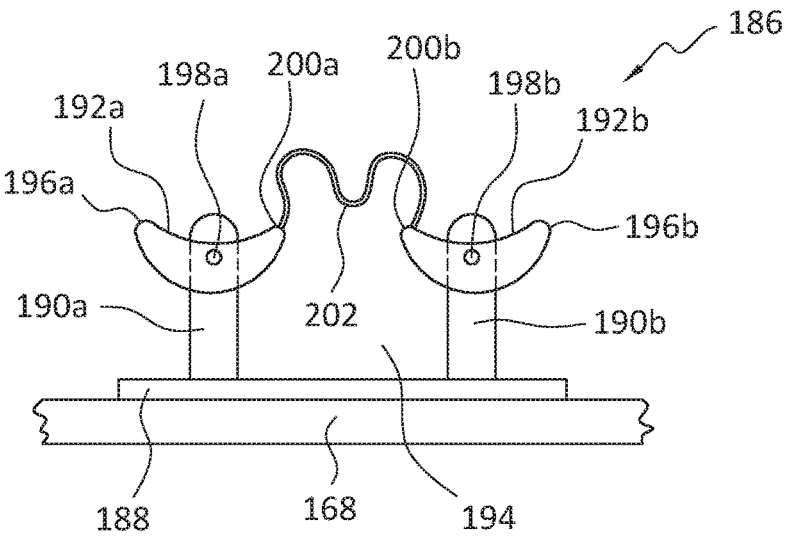
FIG. 5A is a detailed front elevation view of a product gripping support.
Figure 6:
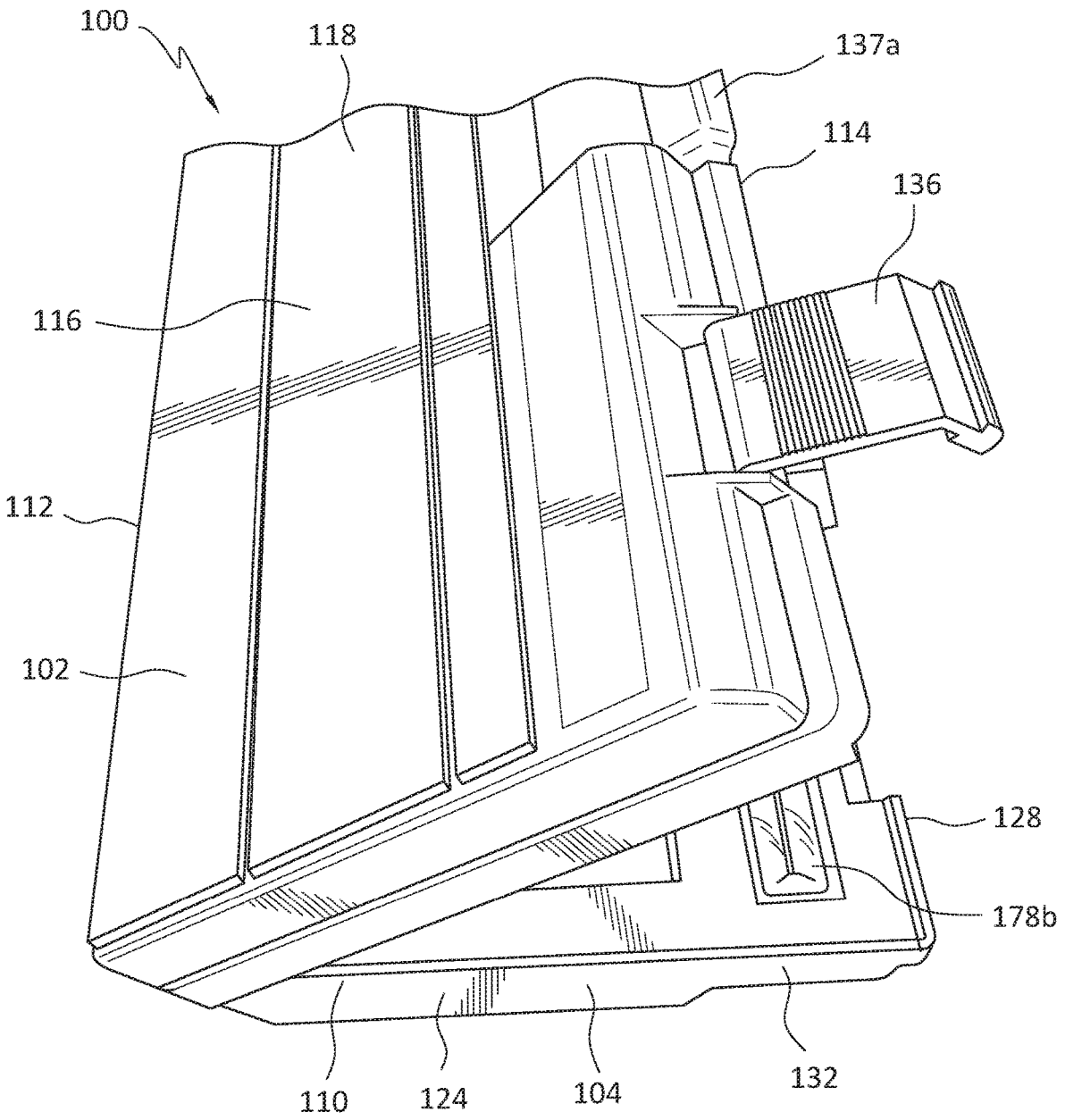
FIG. 6 top perspective view of the present storage and sanitizing case in a partially open configuration.
Figure 7:
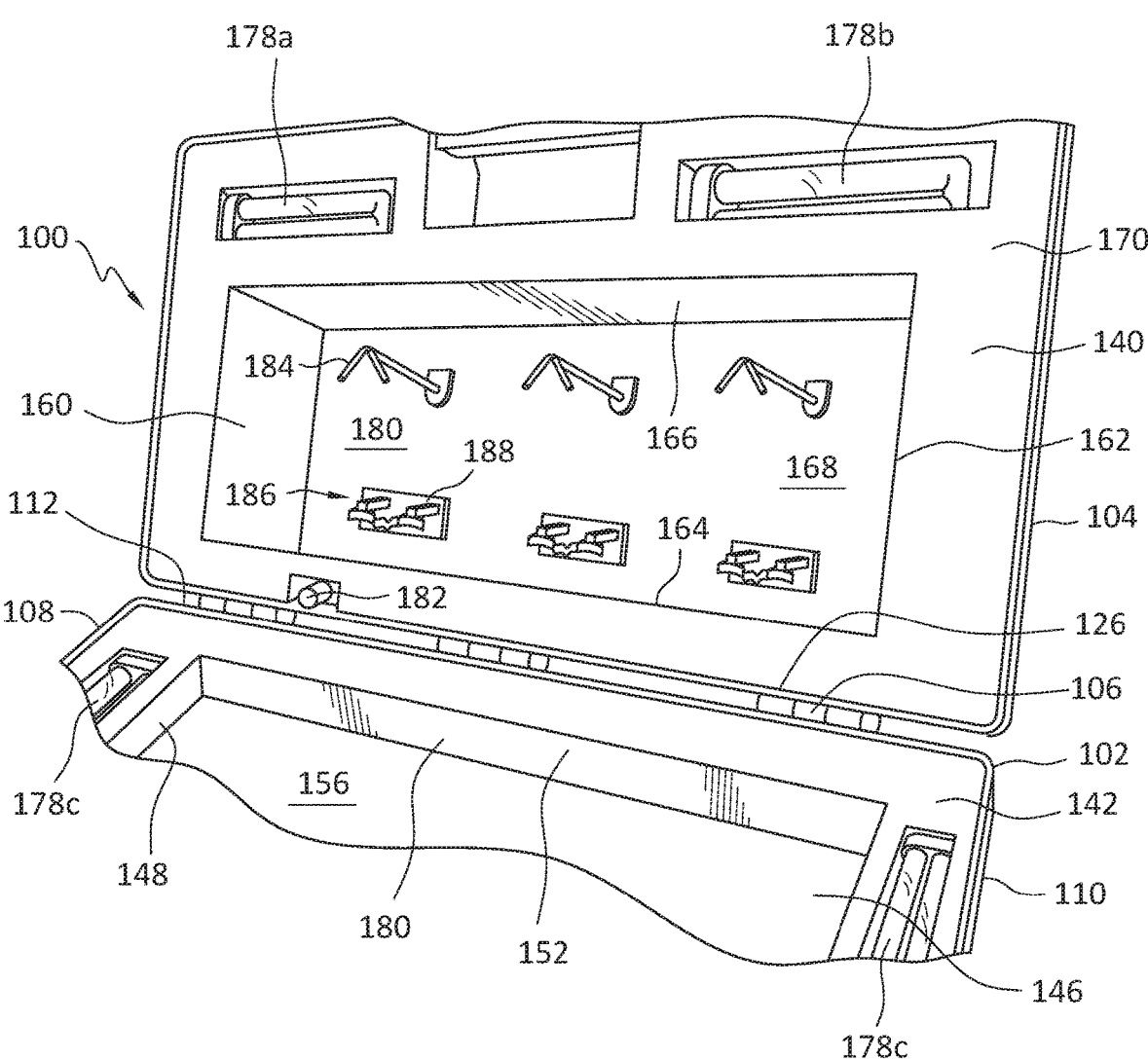
FIG. 7 top perspective view of the present storage and sanitizing case in an open configuration.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

With reference to FIGS. 1 to 7, a storage and sanitizing case 100 for a variety of products is disclosed. The case 100 provides convenient and reliable mechanism for storing, transporting and sanitizing various products, such as, eating utensils, silverware, eyeglasses, barber & salon instruments, etc. In addition to various household products, the present storage and sanitizing case is well suited for storing, transporting, and sanitizing various military related products.

As will be explained below in greater detail, the case 100 is provided with inputs and outputs, as well as sensors and ultraviolet light sources, necessary to sanitize products supported therein. In addition, the case 100 is provided with external indicator lights, for example, a white indicator LED light identifying that the case 100 is charging and a colored LED light that changes color to indicate when the sanitizing process is in progress and when it is finished.

The case 100 has a cover 102 and a base 104. The cover 102 is connected to the base 104 for pivotal movement via a hinge 106 securing the cover 102 to the base 104 along adjacent edges thereof. In accordance with a preferred embodiment, both the cover 102 and the base 104 include a concave construction such that when the case 100 is closed the cover 102 and base 104 define an enclosed space.

More particularly, the base 104 and cover 102 are connected by a hinge 106 allowing for the cover 102 to move between an open configuration where the contents of the case 100 are exposed and a closed configuration where the contents of the case 100 are fully enclosed within the case 100. As will be explained below in greater detail, it is when the case 100 is in its closed configuration that the sanitizing mechanisms may be activated to sanitize the products stored therein.

The cover 102 is substantially rectangular in shape and includes first and second short side walls 108, 110 and first and second long side walls 112, 114 depending from the cover wall 116, as well as an external surface 118 and an interior surface 120 on opposite sides of the cover 102. Similarly, the base 104 is substantially the same shape as the cover 102 and is therefore rectangular in shape and includes first and second short side walls 122, 124 and first and second long side walls 126, 128 depending from the base wall 130, as well as an external surface 132 and an interior surface 134 on opposite sides of the base 104. When in the closed configuration the short side walls 108, 110 and long side walls 112, 114 of the cover 102 align with the short side walls 122, 124 and long side walls 126, 128 of the base 104 with the respective external surfaces 118, 132 of the cover 102 and the base 104 facing away from each other.

As briefly discussed above, a hinge 106 connects the base 104 to cover 102. In accordance with a preferred embodiment, the hinge 106 is formed between the first long side wall 112 of the cover 102 and the first long side wall 126 of the base 104. In this way, the first long side wall 112 of the cover 102 and the first long side wall 126 of the base 104 are held adjacent to each other as the case 100 is moved between its open configuration and its closed configuration. The second long side wall 114 of the cover 102 and the second long side wall 128 of the base 104 are, in contrast, permitted to move toward and away from each other as the case 100 moves between its closed configuration where the second long side wall 114 of the cover 102 and the second long side wall 128 of the base 104 are in contact such that the interior contents of the case 100 are hidden therein and the open configuration where the second long side wall 114 of the cover 102 and the second long side wall 128 of the base 104 are spaced from each other allowing a user to access to the contents of the case 100. The case 100 is further provided with a clasp 136 in the form of a locking mechanism allowing for selective fastening of the case 100 in a closed configuration and opening thereof when desired. The second long side walls 114, 128 of the cover 102 and the base 104 are also provided with a handle members 137a, 137b that meet to form a complete handle when the case 100 is closed.

Access to the products held within the case 100, and separation of the products from the UV lights (preferably UV-C lights as discussed below in more detail), is achieved by providing a base tray 140 within the base 104 for supporting the products within the case 100. A cover tray 142 is provided within the cover 102. The cover tray 142 and base tray 140 align when the case 100 is closed so as to define a cavity 144 in which a product is retained in accordance with the present invention. In accordance with a disclosed embodiment, the cover tray 142 defines a substantially rectangular recess 146 and includes first and second short side walls 148, 150 and first and second long side walls 152, 154 depending from a cover tray top wall 156, as well as an outwardly extending flange 158 structure extending to the edge of the cover 102 so as to completely fill the space defined by the cover 102. Similarly, the base tray 140 is substantially the same shape as the cover tray 142 and is therefore rectangular in shape and includes first and second short side walls 160, 162 and first and second long side walls 164, 166 depending from the base tray bottom wall 168. The base tray 140 also includes an outwardly extending flange structure 170 extending to the edge of the base 104 so as to completely fill the space defined by the base 104. When in the closed configuration the short side walls 148, 150 and long side walls 152, 154 of the cover tray 142 align with the short side walls 160, 162 and long side walls 164, 166 of the base tray 140.

While a configuration of the base and cover trays are disclosed above, it is appreciated the trays may take a variety of forms.

The interior of the case 100 is provided with batteries 172, a power cord 174, an electronic circuit board 176 and ultraviolet lights 178a-d incorporated thereon and secured in position. The elements are positioned between the respective trays 140, 142 and the walls of the base 104 and cover 102. In accordance with a preferred embodiment, the ultraviolet lights 178a-d include four 5 inch ultraviolet bulbs producing UV-C light in the range of 200 nm-400 nm and within a short wave transmissible barrier (for example, synthetic quartz or UV-C films) casings (for example, OSRAM® UV-C/Germicidal lamps that emit 254 nm ultraviolet radiation to purify and disinfect). Two of the ultraviolet lights 178a, 178b are secured along the interior surface 134 of the base 104, between the base 104 and the base tray 140, in alignment with (that is, substantially parallel to) the long side wall 128 of the base 104 adjacent the handle, while the other two ultraviolet lights 178c, 178d are secured along the interior surface 120 of the cover 102 along cover wall 116 in alignment with (that is, substantially parallel to) the short side walls 108, 110 of the cover 102. By manufacturing the trays 140, 142 from quartz or other UV permeable materials and positioning the ultraviolet lights 178a-d between the trays 140, 142 and the cover/base 102, 104, in the manner described, radiation coming from the ultraviolet lights 178a-d is allowed to enter the cavity 144 defined by the base and cover trays 140,142 and effectively sanitize the product within the case 100.

While the surfaces of the base and cover trays 140, 142 in the area adjacent to the ultraviolet lights 178a-d must be left untreated so as to allow for the passage of UV radiation into the cavity 144 defined by the base and cover trays 140, 142, the remaining internal surfaces of the base and cover trays 140, 142 defining the cavity 144 (for example, in accordance with the disclosed embodiment, the first and second long side walls 152, 154 of the cover tray 142, the cover tray top wall 156, the first and second short side walls 160, 162 of the base tray 140, the second long side wall 166 of the base tray 140, and the base tray bottom wall 168) are covered in a UV reflective material 180 to enhance the transmission of the UV-C light to the surfaces of the product requiring sanitizing. In accordance with a preferred embodiment, the material is COILZAK® as manufactured by Alcoa, which is a metal sheet of aluminum or aluminum base alloy.

The electronic circuit board 176 is connected to the ultraviolet lights 178a-d as well as the batteries 172 or the power cord 174 via power wire (not shown). An actuator 182 transmits a signal to the circuit board 176 when the cover 102 is closed upon the base 104 causing power to be applied to the ultraviolet lights 178a-d. The signal is only transmitted when the case 100 is closed and opening of the case 100 interrupts the signal causing power to the ultraviolet lights 178a-d to cease. The signal initiates power from the electronic circuit board 176 to the ultraviolet lights 178a-d for a preset time period. The electronic circuit board includes a timer 176t which controls the timing for the application of power to the ultraviolet lights 178a-d. In a preferred embodiment, ultraviolet light is illuminated for 2-5 minutes.

The case 100 is intended for sanitizing, supporting and transporting a variety of products. As such, it is important that the case 100 include a versatile support mechanism. In accordance with a preferred embodiment, the case 100 is provided with a plurality of vertically oriented support posts 184 upon which products are secured. These posts 184 are preferably composed of quartz, which allows for the passage of UV-C light therethrough and, therefore does not hinder the sanitizing process.

In addition, the case 100 is provided with a plurality of product gripping supports 186 (see FIGS. 1, 5, 5A, and 7. Each of the plurality of product gripping supports 186 includes a support base 188 fixedly secured to the base tray

140 of the case 100 and first and second support arms 190a, 190b extending upwardly within the case 100 and to which first and second bracket arms 192a, 192b are pivotally secured. The space between the first and second bracket arms 192a, 192b defines the product recess 194. The first ends 196a, 196b of the first and second bracket arms 192a, 192b are free, the centers 198a, 198b of the first and second bracket arms 192a, 192b are pivotally secured to the first and second support arms 190a, 190b, and the second ends 200a, 200b are connected by a securing band 202 extending therebetween. A product is attached to the product gripping supports 186 by pressing the product against the securing band 202 and pressing the product into the product recess 200. The pivoting first and second bracket arms 192a, 192b allow the securing band 202 to pivot when the product is pressed into the product recess 194. Wherein, when the securing band 202 is compressed, then the product enters the product recess 194. The placement of the product into the product recess 194 creates a series of forces that effectively hold the product in the product recess 194, thereby effectively retaining the product in the product recess 194. Upon pulling of the product from the product recess 194, these forces are overcome and product is released.

In accordance with a preferred embodiment, and as with the posts 184, all of the rigid components (that is, the support base 188, the first and second support arms 190a, 190b, and the first and second bracket arms 192a, 192b) of the product gripping supports 186 are made of quartz so as to allow for the passage of UV-C light therethrough and not hinder the sanitizing process. The securing band 202 is made of a UV permeable resilient material, for example, UV-C stabilized flexible band, sling, or strap.

The supporting structures are positioned adjacent to each and are oriented such that eyeglasses, silverware, or other products requiring sanitizing may be easily positioned therein.

In accordance with a preferred embodiment, the ultraviolet lights function with the following characteristics:

Wattage: 0.3 W±15%
Voltage: 160V±8
Power: 1.7 mA
254 nm output*: 260 uW/cm$^2$ (at surface)
Stability: 5 min
Life: 10000 hrs.
 *The radiant efficiency of the ultraviolet light measured at a wavelength of 254 nm based upon the fact 254 nm wavelength ultraviolet light is effective in killing bacterial, mold, and viral agents An ultraviolet light with these characteristics produces highly desirable results as shown in Table A.

TABLE A

|  | Kill rate (uW · sec/cm^2) | Time to kill at 1 cm target distance (seconds) |
| --- | --- | --- |
| *Escherichia coli* | 6600 | 1.6 |
| *Staphylococcus aureus* | 6600 | 1.6 |
| *Streptococcus lactis* | 8800 | 2.2 |
| Infectious hepatitis | 8000 | 2.0 |
| Influenza | 6600 | 1.6 |
| Virus | 6600 | 2.5-3.0 |

Figure 8:
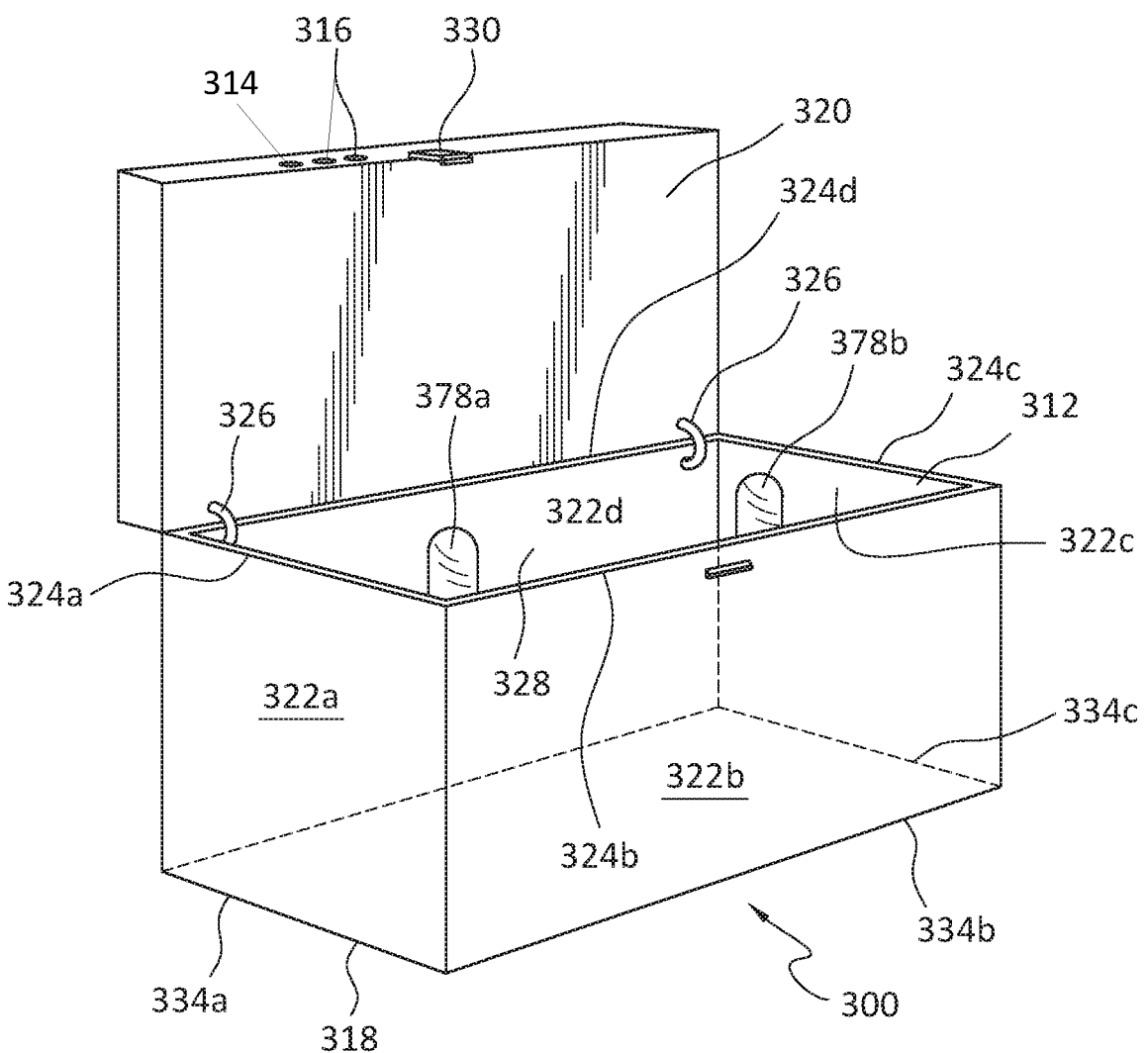
FIG. 8 is perspective view of another embodiment of the present storage and sanitizing case in its open configuration.
Figure 9:
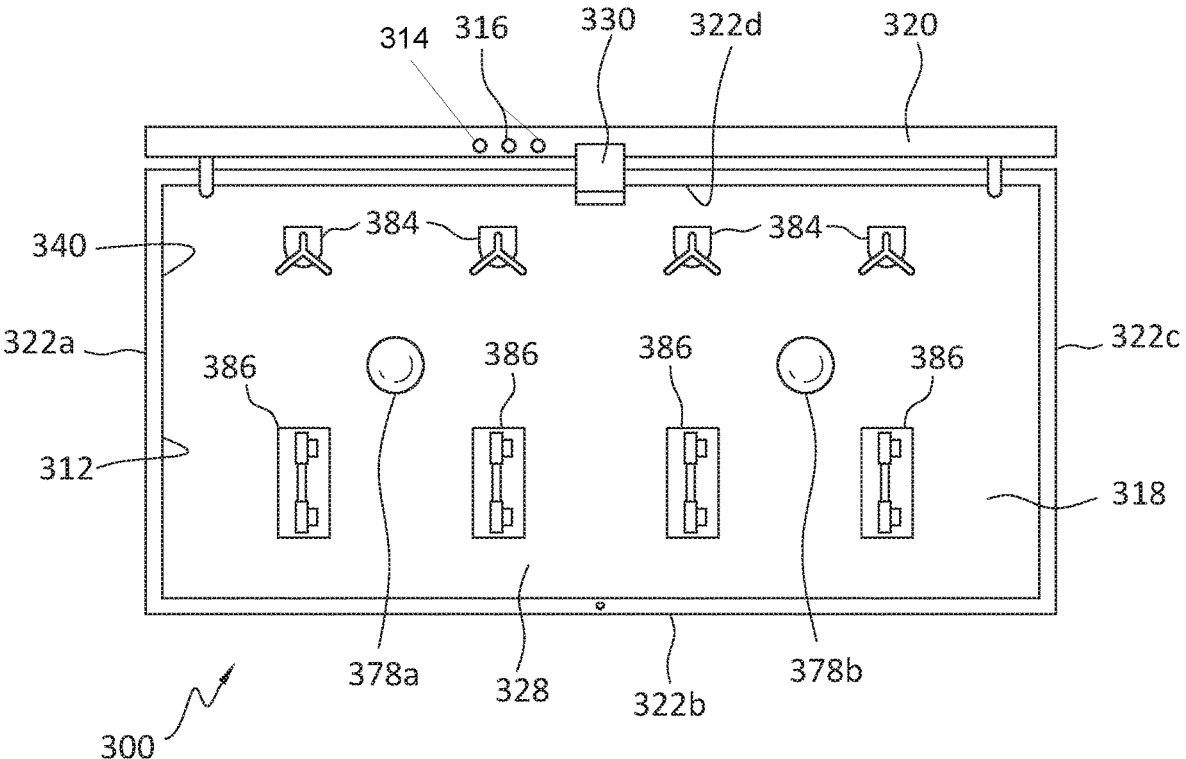
FIG. 9 is a top plan view of the storage and sanitizing case shown in FIG. 8 in its open configuration.
Figure 10:
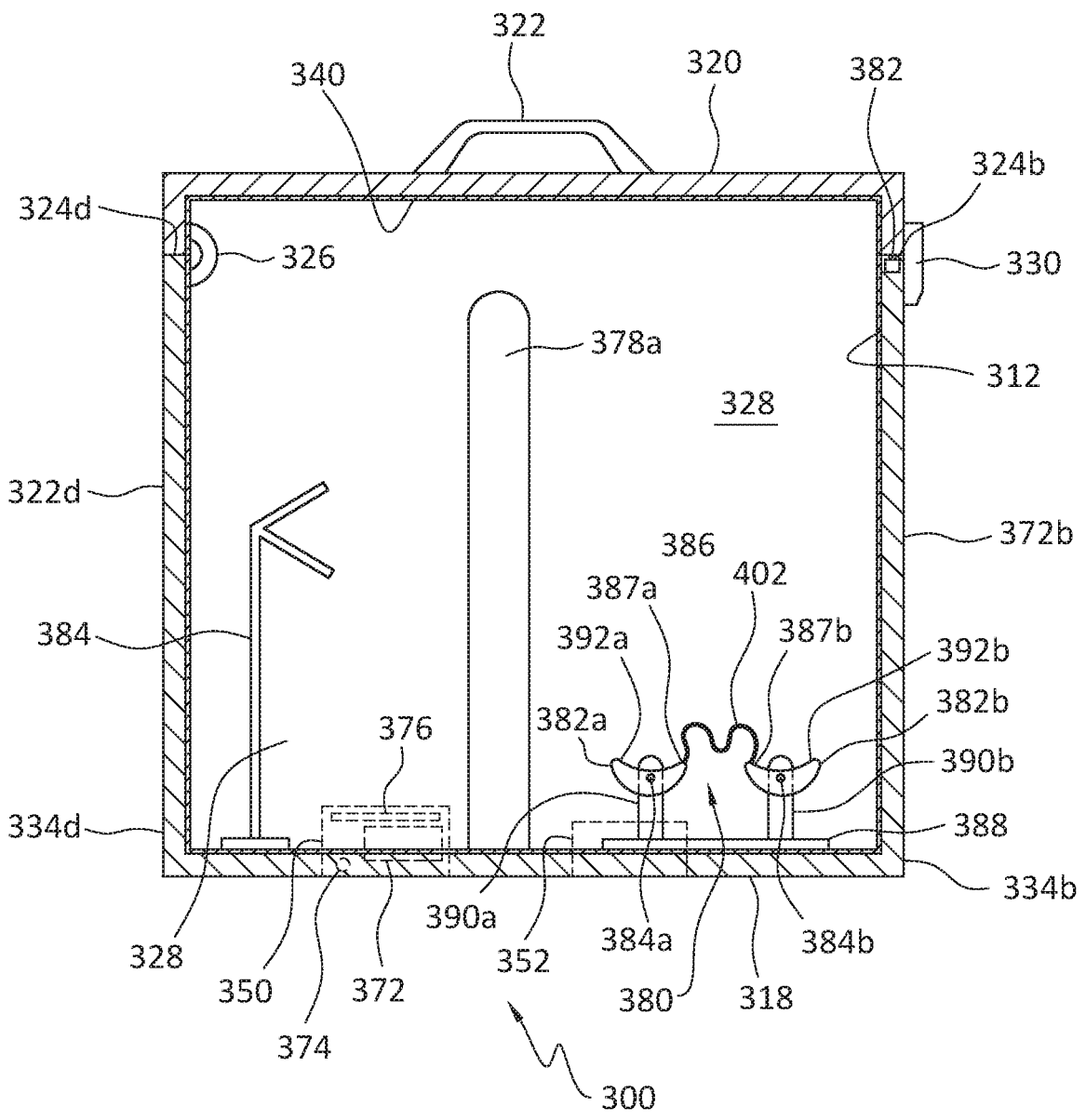
FIG. 10 is a cross sectional view of the storage and sanitizing case shown in FIG. 8 in its closed configuration.
Figure 11:
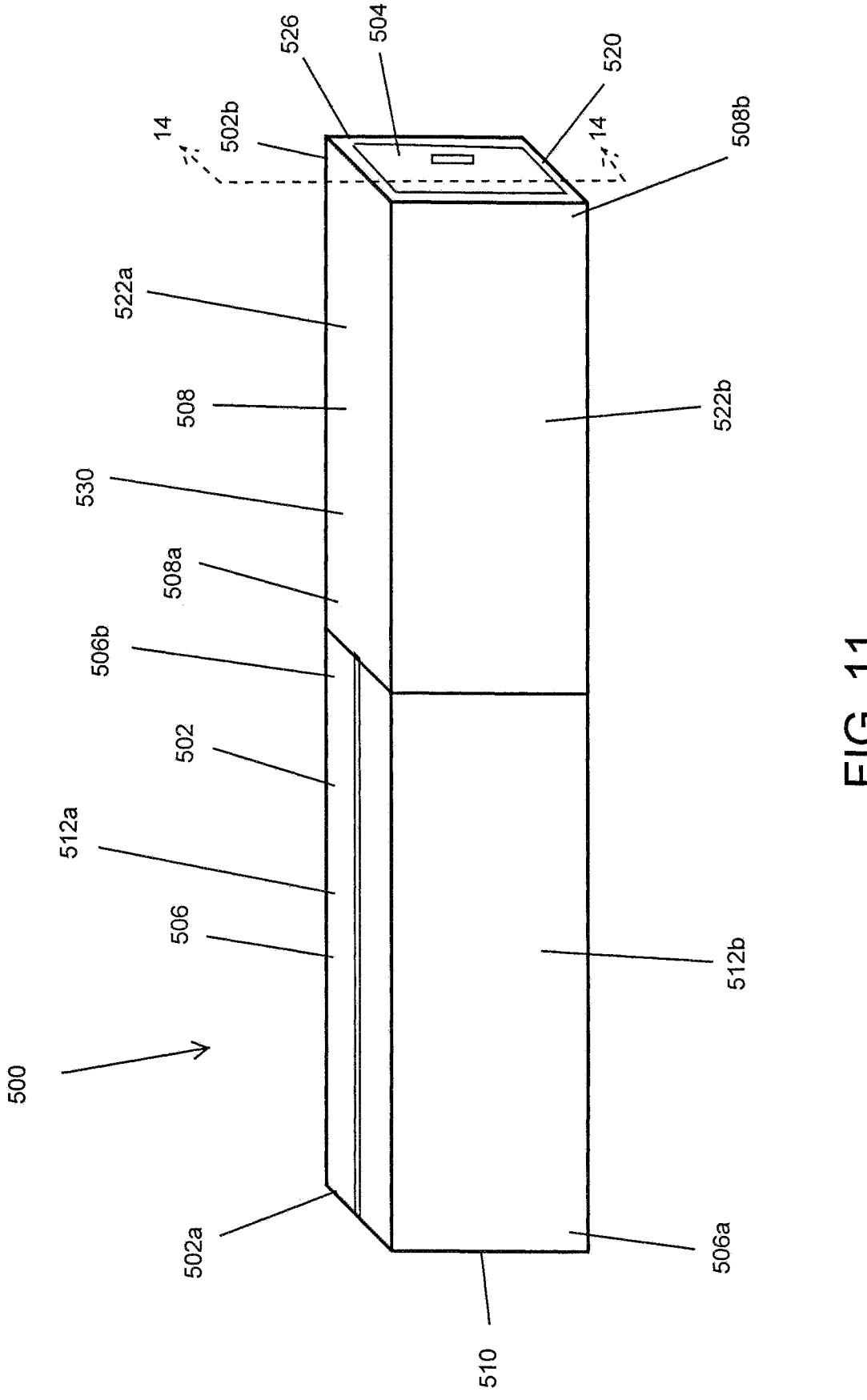
FIGS. 11 and 12 are perspective views of an alternate embodiment viewing the storage and sanitizing case from opposite directions, wherein the storage and sanitizing case is shown in its use configuration.
Figure 12:
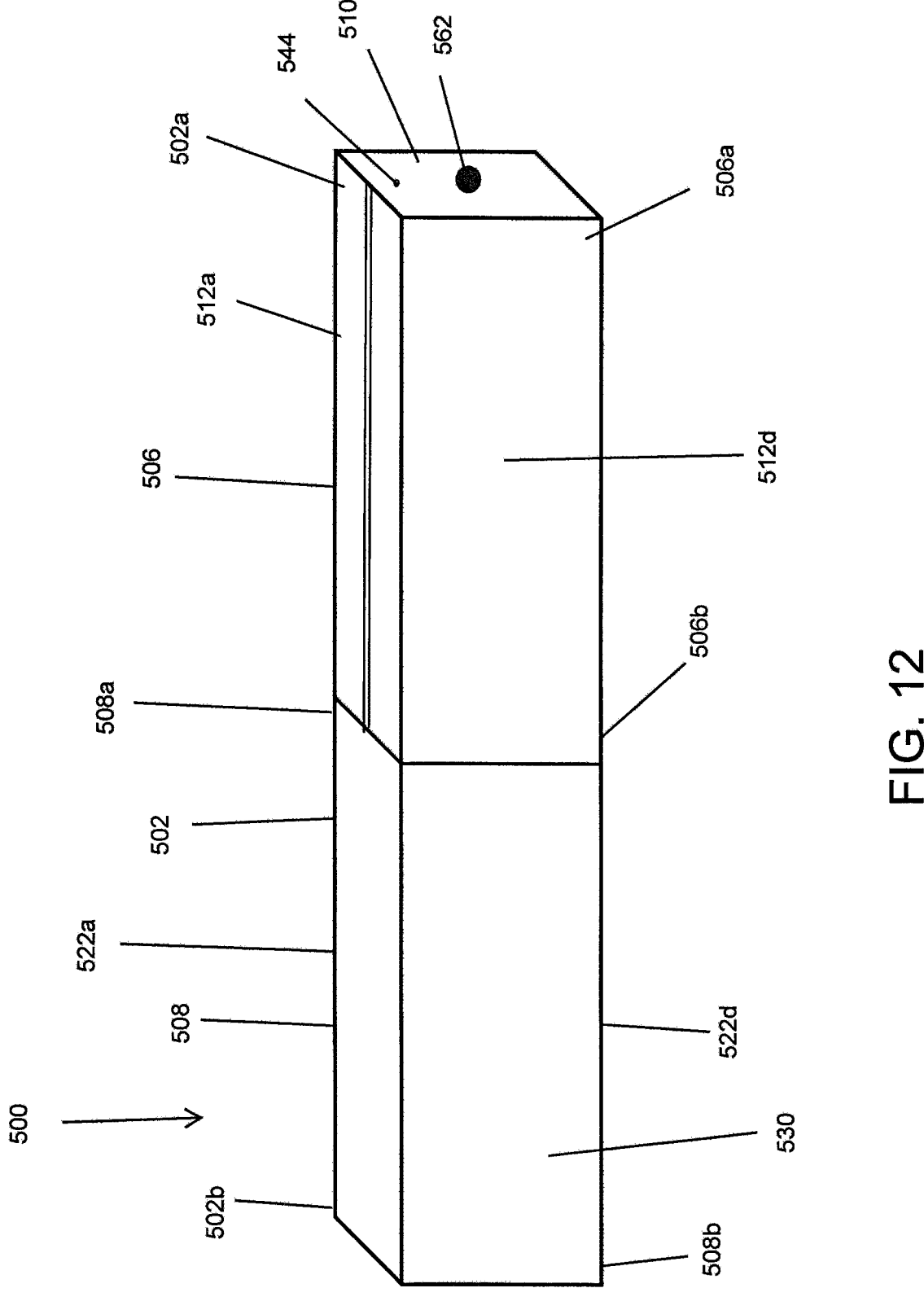
Figure 13:
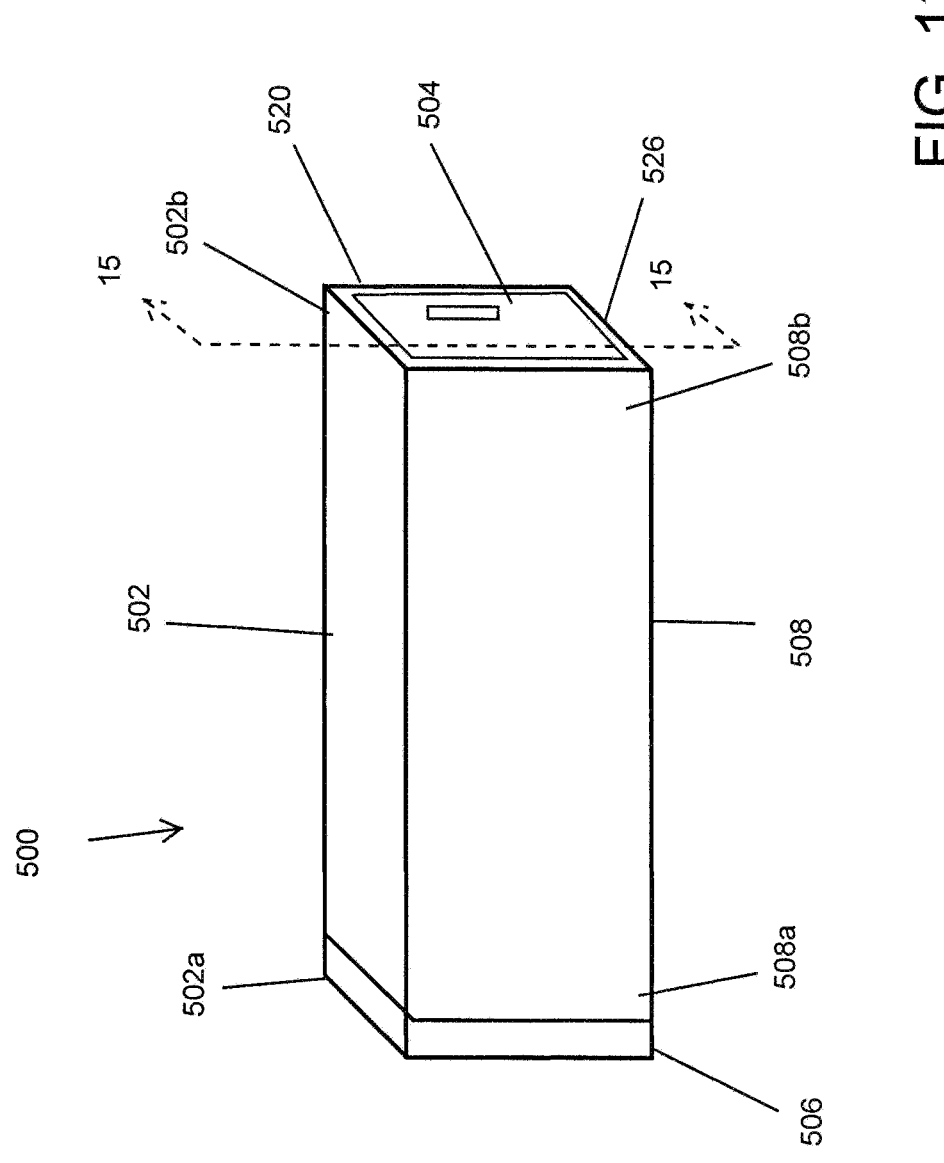
FIG. 13 is a perspective view of the embodiment shown in FIGS. 11 and 12 with the storage and sanitizing case shown in its storage configuration.
Figure 14:
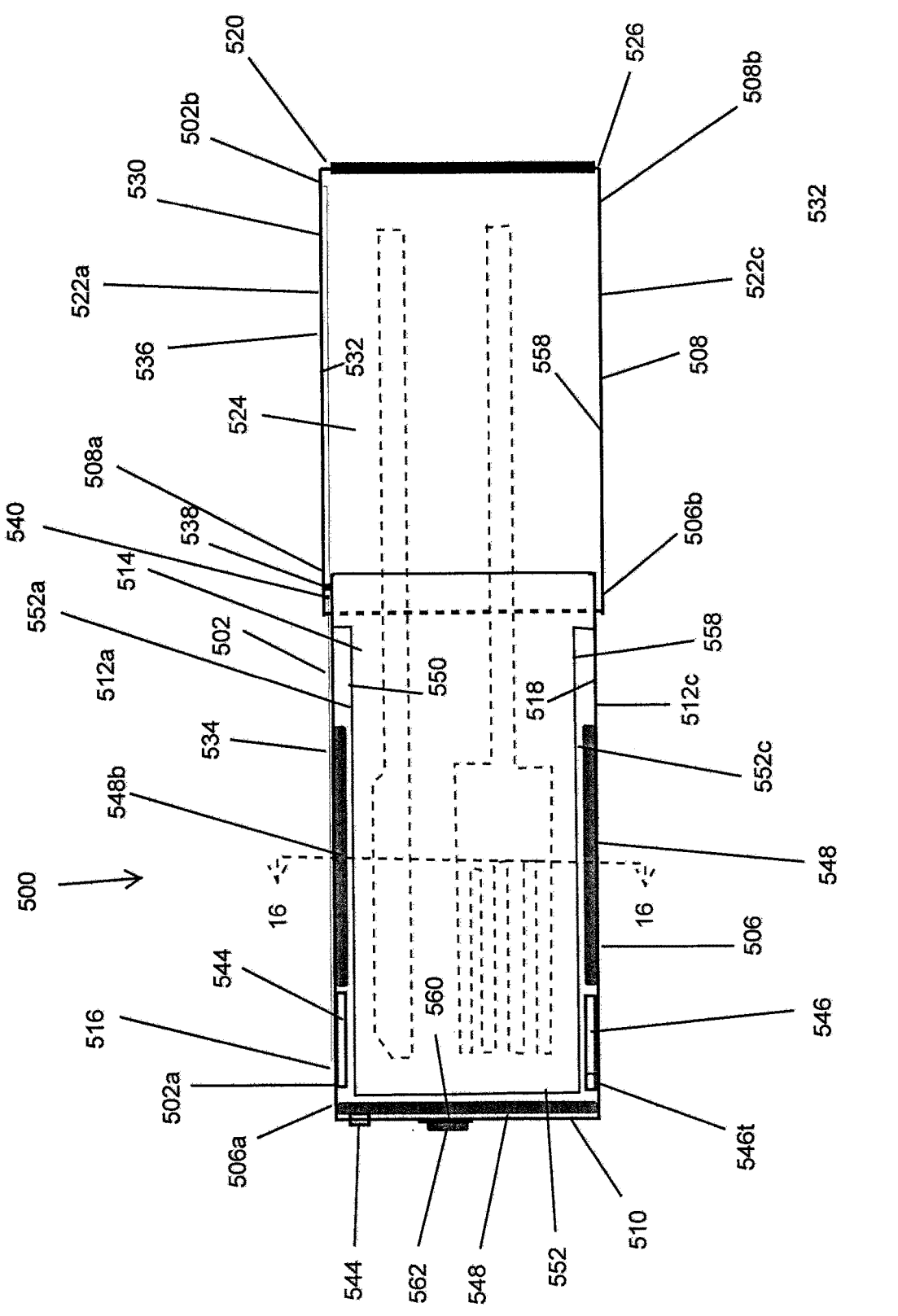
FIG. 14 is a cross sectional view along the line 14-14 in FIG. 11.
Figure 15:
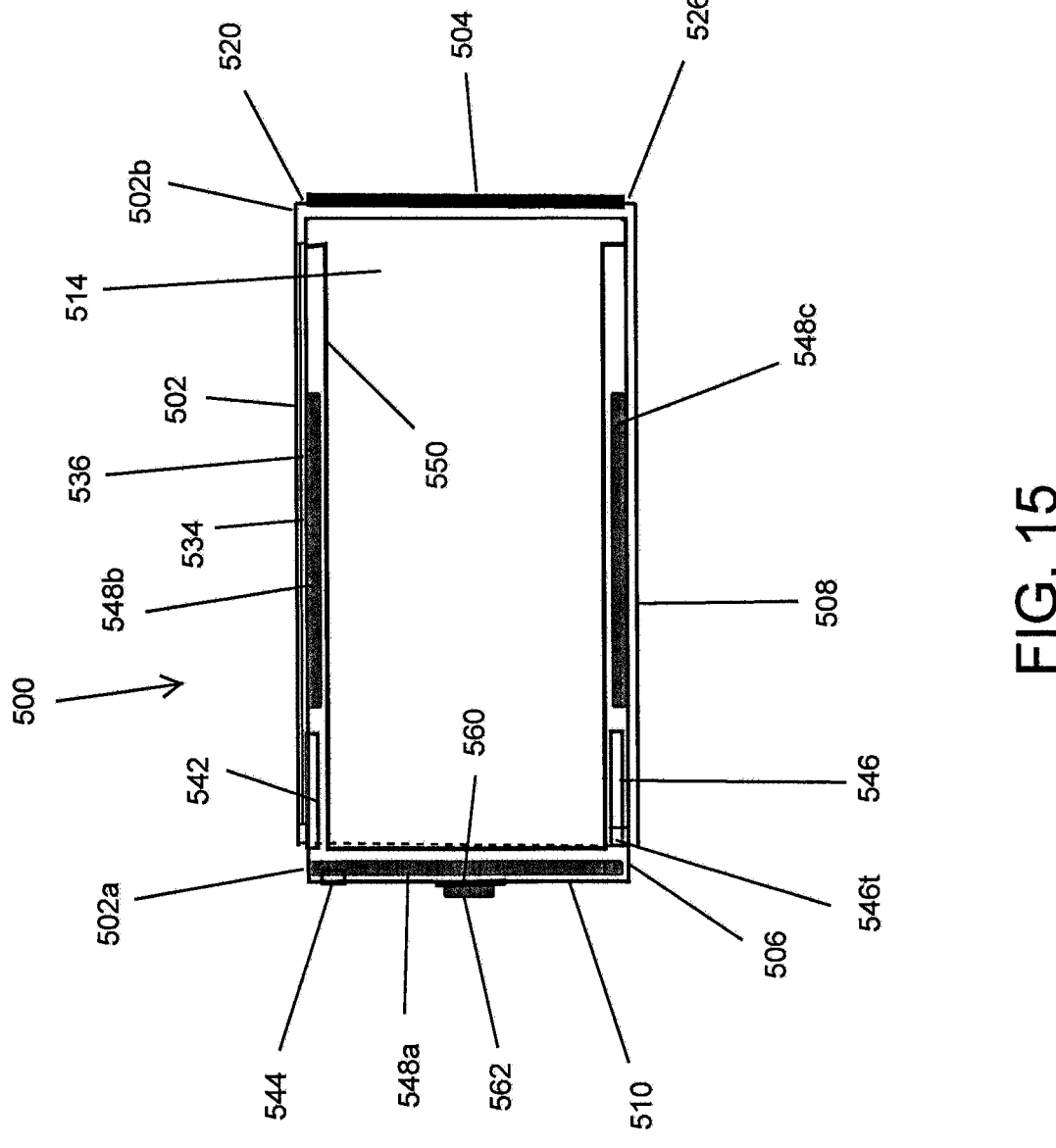
FIG. 15 is a cross sectional view along the line 15-15 in FIG. 13.
Figure 16:
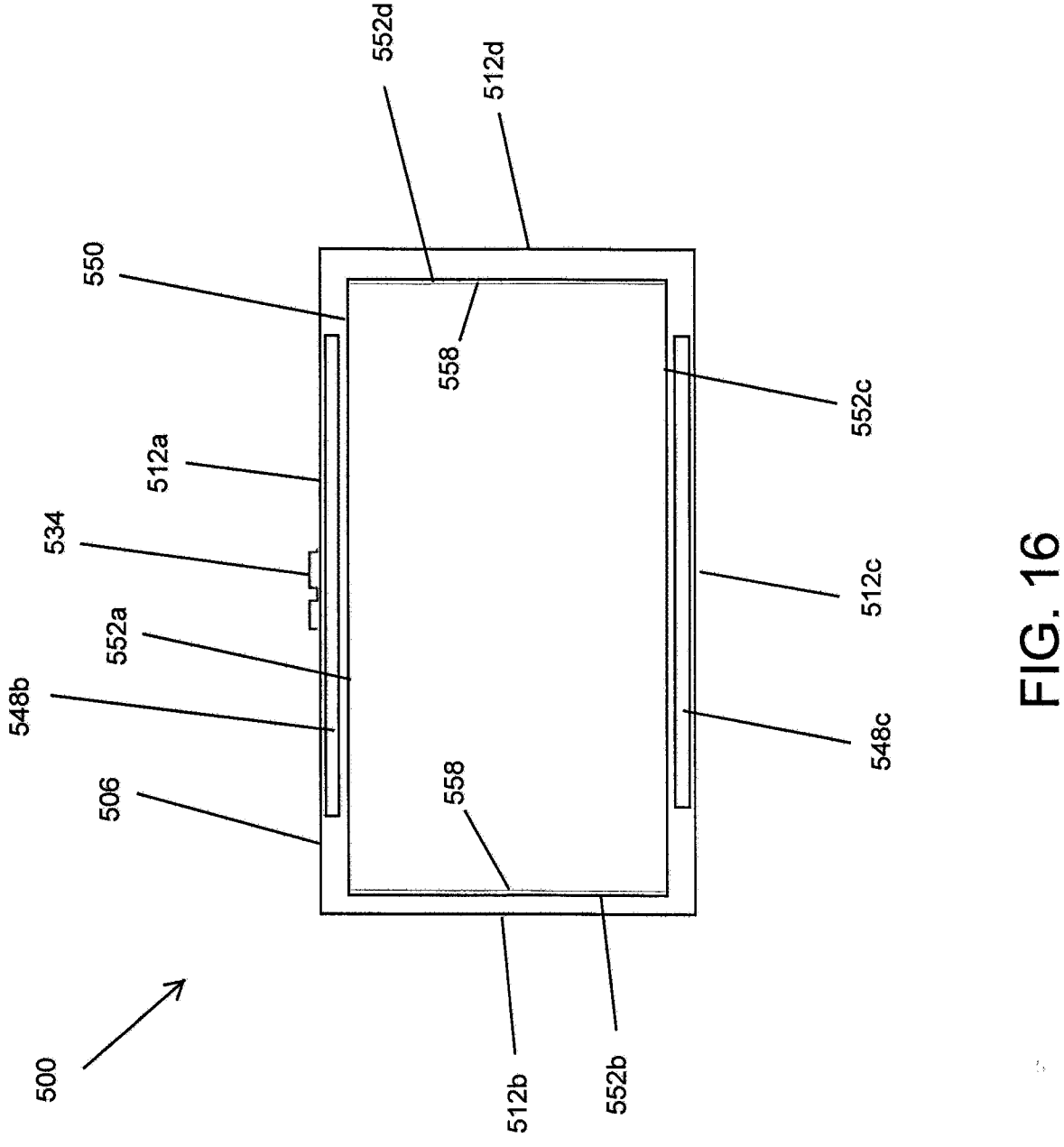
FIG. 16 is a cross sectional view along the line 16-16 in FIG. 14 (without eating utensils).

With reference to FIGS. 8, 9, and 10, and in accordance with an alternate embodiment, a storage and sanitizing case 300 is disclosed. The case 300 provides a convenient and reliable mechanism for storing, transporting and sanitizing various products, as well as associated accessories. As such, it is appreciated the case 300 may be configured for storing the products and/or their associated accessories in either an assembled or unassembled configuration. In addition to storing the products and/or their associated accessories, the present case 300 is also well suited for transporting and sanitizing the products and/or their associated accessories.

The case 300 includes a sanitizing container 312 and sanitizing components that are used in the sanitizing process employed in accordance with the present invention for the treatment of products placed therein. As will be explained below in greater detail, the sanitizing container 312 is provided with inputs and outputs, as well as sensors and ultraviolet light sources, necessary to sanitize products supported therein. In addition, the sanitizing container 312 is provided with external indicator lights, for example, a white indicator LED light 314 identifying that the sanitizing container 312 is charging and a colored LED light 316 that changes color to indicate when the sanitizing process is in progress and when it is finished.

The sanitizing container 312 includes a base 318 and a top 320, with a plurality of upstanding side walls 322*a*-*d* extending between the base 318 and the top 320. In accordance with a preferred embodiment, the base 318 is rectangular shaped. A first upstanding side wall 322*a*, a second upstanding side wall 322*b*, a third upstanding side wall 322*c*, and a fourth upstanding side wall 322*d* are fixedly secured to and respectively extending upwardly from edges of the rectangular shaped base 318. The top 320 is similarly rectangular shaped and has edges 320*a*-*d* thereof aligned with the upper edges 324*a*-*d* of the respective side walls 322*a*-*d* when the top 320 is in its closed configuration. It is appreciated that although the present invention is disclosed herein with a rectangular shape, the sanitizing container 312 may take various shapes depending upon the specifics of the product intended for use in conjunction with the sanitizing container 312.

The top 320 is hinged 326 to the fourth upstanding side wall 322*d* in a manner allowing for opening and closing thereof for access to the internal cavity 328 defined by the sanitizing container 312. The top 320 includes a clasp 330 in the form of a locking mechanism allowing for selective fastening of the top 320 to the remainder of the container 312 in a closed configuration and opening thereof when desired. The top 320 is also provided with a handle 332.

The sanitizing container 312, including the housing and various internal structural components, itself is primarily constructed from plastic, for example, ABS (acrylonitrile butadiene styrene) plastic, although it is appreciated the sanitizing container 312 may be constructed from various materials depending upon cost, weight, manufacturing considerations, and compatibility with UV-C lighting.

Each of the first, second, third, and fourth upstanding side walls 322*a*-*d* includes a lower end 334*a*-*d* secured to an edge of the base 318. The first, second, third, and fourth upstanding side walls 322*a*-*d* are fixedly attached to each other along their respective adjacent upwardly extending edges. The internal surfaces of the upstanding side walls 322*a*-*d*, top 320, and base 318, that is, those portions of the upstanding side walls 322*a*-*d*, top 320, and base 318 defining the cavity 328, are covered in a UV reflective material 340 to enhance the transmission of the UV-C light to the surfaces of the product requiring sanitizing. In accordance with a preferred embodiment, the material is COILZAK® as manufactured by Alcoa, which is a metal sheet of aluminum or aluminum base alloy.

As with the prior embodiment, the case 300 also includes sanitizing components contained within the sanitizing container 312. The sanitizing components include an electrical power control assembly 350 and an ultraviolet light assembly 352. The electrical power control assembly 350 is composed of batteries 372, retractable power cord 374, and an electronic circuit board 376.

As to the ultraviolet light assembly 352, it is composed of a plurality of ultraviolet lights 378*a*, 378*b* producing UV-C light in the range of 200 nm-400 nm. In accordance with a preferred embodiment, each of the ultraviolet lights includes a 5 inch ultraviolet bulb within a short wave transmissible barrier (for example, synthetic quartz or UV-C films) casing. The ultraviolet lights 378*a*, 378*b* are centrally mounted within the cavity 328 so as to extend upwardly from the base 318. The electronic circuit board 376 is connected to the ultraviolet lights 378*a*, 378*b*, batteries 372, and the power cord 374 via conventional wiring (not shown). An actuator 382 transmits a signal to the circuit board 376 when the top 320 is closed causing power to be applied to the ultraviolet lights 378*a*, 378*b*. The signal is only transmitted when the top 320 of the case 300 is closed and opening of the top 320 of the case 300 interrupts the signal causing power to the ultraviolet lights 378*a*, 378*b* to cease. The signal initiates power from the electronic circuit board 376 to the ultraviolet lights 378*a*, 378*b* for a preset time period. The electronic circuit board 376 includes a timer which controls the timing for the application of power to the ultraviolet lights 378*a*, 378*b*.

As with the prior embodiment, the case 300 is intended for sanitizing, supporting, and transporting a variety of products. As such, it is important that the case 300 include a versatile support mechanism. In accordance with a preferred embodiment, the sanitizing container 312 is provided with a plurality of vertically oriented support posts 384 upon which products are secured. These posts 384 are preferably composed of quartz, which allows for the passage of UV-C light therethrough and, therefore does not hinder the sanitizing process.

In addition, the case 300 is provided with a plurality of product gripping supports 386. Each of the plurality of product gripping supports 386 includes a support base 388 fixedly secured to the base 318 of the sanitizing container 312 and first and second support arms 390*a*, 390*b* extending upwardly within the sanitizing container 312 and to which first and second bracket arms 392*a*, 392*b* are pivotally secured. The space between the first and second bracket arms 392*a*, 392*b* defines the product recess 380. The first ends 382*a*, 382*b* of the first and second bracket arms 392*a*, 392*b* are free, the centers 384*a*, 384*b* of the first and second bracket arms 392*a*, 392*b* are pivotally secured to the first and second support arms 390*a*, 390*b*, and the second ends 387*a*, 387*b* are connected by a securing band 402 extending therebetween. Referring to FIG. 10, a product is attached to the product gripping supports 386 by pressing the product against the securing band 402 and pressing the product into the product recess 380. The pivoting first and second bracket arms 392*a*, 392*b* allow the securing band 402 to pivot when the product is pressed into the product recess 380. Wherein, when the securing band 402 is compressed, then the product enters the product recess 380. The placement of the product into the product recess 380 creates a series of forces that effectively hold the product in the product recess 380, thereby effectively retaining the product in the product recess 380. Upon pulling of the product from the product recess 380, these forces are overcome and the product is released.

In accordance with a preferred embodiment, and as with the posts 384, all of the rigid components (that is, the support base 388, the first and second support arms 390*a*, 390*b*, and the first and second bracket arms 392*a*, 392*b*) of the product gripping supports 386 are made of quartz so as to allow for the passage of UV-C light therethrough and not hinder the sanitizing process. The securing band 402 is made of a UV permeable resilient material, for example, UV-C stabilized flexible band, sling, or strap.

The supporting structures are positioned adjacent to each and are oriented such that eyeglasses, silverware, or other products requiring sanitizing may be easily positioned therein.

In accordance with an alternate embodiment as shown with reference to FIGS. 11 to 16, a highly portable storage and sanitizing case 500 specifically adapted for sanitizing silverware or eating utensils is disclosed. In accordance with a disclosed embodiment, the case 500 including a telescopically expandable housing 502 including a door 504 that is selectively opened to allow for placement of silverware or other eating utensils within the case 500 for treatment in accordance with the present invention. While this embodiment is disclosed for use in conjunction with silverware and eating utensils, it is contemplated it may also be used with eyeglasses, credit cards, keys, ear pods (and other headphones), etc.

The expandable housing 502 is substantially rectangular in shape when viewed along a cross section perpendicularly oriented relative to the longitudinal axis that extends from the first end 502*a* of the expandable housing 502 to second end 502*b* of the expandable housing 502. The first end 502*a* is closed and the second end 502*b* includes the selectively openable door 504.

As the expandable housing 502 includes a telescopic construction it is composed of a first end member 506 and a second end member 508. The first end member 506 is substantially rectangular in shape when viewed along a cross section perpendicularly oriented relative to the longitudinal axis that extends from the first end 506*a* of the first end member 506 to the second end 506*b* of the first end member 506. The first end member 506 includes a base member 510 from which first, second, third, and fourth side walls 512*a*-*d* extend so as to define a cavity 514. As such, the first end member 506 includes a first end 506*a* that is closed by the base member 510 and an open second end 506*b* shaped and dimensioned to allow for the passage of silverware therethrough and into a cavity defined by the base member and the first, second, third, and fourth side walls. The first end member 506 includes an external surface 516 and an interior surface 518 defining the cavity 514.

The second end member 508 is also substantially rectangular in shape when viewed along a cross section perpendicularly oriented relative to the longitudinal axis that extends from the first end 508*a* of the second end member 508 to the second end 508*b* of the second end member 508. The second end member 508 includes a cross sectional profile slightly larger than the first end member 506 such that the second end member 508 moves over the first end member 506 in a telescopic manner as discussed below so as to allow the expandable housing 502 to be configured between its storage configuration (see FIGS. 13 and 15) with the second end member 508 substantially overlapping with the first end member 506 and the use configuration (see FIGS. 11, 12, and 14) with the second end member 508 just slightly overlapping with the first end member 506 such that the expandable housing 502 is of a length sufficient to position silverware therein.

The second end member 508 includes a base door assembly 520 from which first, second, third, and fourth side walls

522*a*-*d* extend so as to define a cavity 524. The base door assembly 520 includes a frame member 526 to which the first, second, third, and fourth side walls 522*a*-*d* are secured and a cover 528 secured to cover the interior space defined by the frame member 526. The cover 528 is pivotally secured to the frame member 526 so as to allow the base door assembly 520 to be selectively opened when one desires to insert silverware within the expandable housing 502.

As such, the second end member 508 includes an open first end 508*a* and a selectively closed second end 508*b* defined by the base door assembly 520. As with the first end member 506, the second end member 508 is shaped and dimensioned to allow for the passage of silverware therethrough and into cavity 524 defined by the base door assembly 520 and the first, second, third, and fourth side walls 522*a*-*d*. The first end member 506 includes an external surface 530 and an interior surface 532 defining the cavity 524.

Relative positioning and controlled movement of the first end member 506 and the second end member 508 is achieved by providing external surface 516 of the first end member 506 with rail members 534 upon which rail members 536 of the interior surface 532 of the second end member 508 ride. While rail members 534, 536 are disclosed in accordance with the disclosed embodiment, other guiding structures may be provided to control the movement of the first end member 506 and second end member 508. In addition, the external surface 516 of the first end member 506 includes an abutment member 538 adjacent the second end 506*b* of the first end member 506 and the second end member 508 includes an abutment member 540 adjacent the first end 508*a* of the second end member 508 so as to limit movement of the second end member 508 relative to the first end member 506 when the fully extended position is achieved.

As with the prior embodiments, the case 500 is provided with batteries 542, a power adapter port 544 for charging the batteries 542 in a known manner, an electronic circuit board 546, and ultraviolet lights 548*a*-*c*, all connected via wiring (not shown) in a conventional manner. The elements are positioned between an interior tray 550 formed within the first end member 506 and the interior surface 518 of the first end member 506. The interior tray 550 is shaped and dimensioned to conform the with interior surface 518 of the first end member 506 such that the various elements discussed herein may be positioned between the interior tray 550 and the interior surface 518 of the first end member 506. The interior tray 550 therefore includes a base member 552 from which first, second, third, and fourth side walls 554*a*-*d* extend.

In accordance with a preferred embodiment, three ultraviolet lights 548*a*-*c* are provided. The ultraviolet lights 548*a*-*c* produce UV-C light in the range of 200 nm-400 nm. The first ultraviolet light 548*a* is positioned between the base member 510 of the first end member 506 and the base member 552 of the interior tray 550, the second ultraviolet light 548*b* is positioned between the first side wall 512*a* of the first end member 506 and the first side wall 554*a* of the interior tray 550 in alignment with (that is, substantially parallel to) the first side wall 512*a* and extending along the longitudinal axis of the expandable housing 502, and the third ultraviolet light 548*c* is positioned between the third side wall 512*c* of the first end member 506 and the third side wall 554*c* of the interior tray 550 in alignment with (that is, substantially parallel to) the third side wall 512*c* and extending along the longitudinal axis of the expandable housing

502. By manufacturing the tray 550 from quartz or other UV permeable materials and positioning of the ultraviolet lights 548*a-c* between the tray 550 and the first end member 506, in the manner described, radiation coming from the ultraviolet lights 548*a-c* is allowed to enter the cavity 556 defined by the cavities 514, 524 of first and second end members 506, 508 and effectively sanitize the product.

While the surfaces of the tray 550 in the area adjacent to the ultraviolet lights 548*a-c* must be left untreated so as to allow for the passage of UV radiation into the cavity 556 defined by the first and second end members 506, 508, the remaining internal surfaces of the tray 550, first end member 506, and second end member 508 are covered with UV reflective material 558 to enhance the transmission of the UV-C light to the surfaces of the product requiring sanitizing. In accordance with a preferred embodiment, the material is COILZAK® as manufactured by Alcoa, which is a metal sheet of aluminum or aluminum base alloy.

The electronic circuit board 546 is connected to the ultraviolet lights 548*a-c* as well as the batteries 542 via power wire (not shown). An actuator 560 transmits a signal to the circuit board 546 when the actuator button 562 is pressed causing power to be applied to the ultraviolet lights 548*a-c*. The signal is only transmitted when the case 500 is fully extended to its use orientation and the cover 528 is closed. Opening of the cover 528 interrupts the signal causing power to the ultraviolet lights 548*a-c* to cease. The signal initiates power from the electronic circuit board 546 to the ultraviolet lights 548*a-c* for a preset time period. The electronic circuit board 546 includes a timer 546*t* which controls the timing for the application of power to the ultraviolet lights 548*a-c*. In a preferred embodiment, ultraviolet light is illuminated for 2-5 minutes.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A storage and sanitizing case, comprising:
a cover and a base, the cover is connected to the base for pivotal movement relative thereto, the cover including side walls and the base includes side walls;
a cover tray positioned within the cover, the cover tray comprises a UV permeable material and includes a recess, first and second short side walls and first and second long side walls depending from a cover tray top wall, and an outwardly extending flange structure extending to an edge of the cover so as to completely fill space defined by the cover;
a base tray within the base for supporting products within the case, the base tray comprises a UV permeable material and includes first and second short side walls and first and second long side walls depending from a base tray bottom wall, and an outwardly extending flange structure extending to an edge of the base so as to completely fill space defined by the base, wherein the cover tray and base tray align when the case is closed so as to define a cavity in which a product is retained, wherein the short side walls and long side walls of the cover tray align with the short side walls and long side walls of the base tray;
internal surfaces of the cover tray and the base tray are covered in a UV reflective material to enhance transmission;
a plurality of product gripping supports comprising a UV permeable material and being secured to the base tray, each of the plurality of gripping supports further includes a support base and first and second support arms extending upwardly, first and second bracket arms are respectively pivotally secured to the first and second support arms, and a securing band extends between the first and second bracket arms;
an electronic circuit board and an actuator connected to the circuit board; and
at least four ultraviolet lights connected to the electronic circuit board wherein the actuator transmits a signal to the circuit board when the cover is closed upon the base causing power to be applied to the ultraviolet lights, the at least four ultraviolet lights including two ultraviolet lights secured along an interior surface of the base, between the base and the first long side wall of the base tray, in parallel alignment with the first and second long side walls of the base tray, and two ultraviolet lights respectively secured along an interior surface of the cover along a cover wall in parallel alignment with opposed the first and second short side walls of the cover, wherein surfaces of the base tray and the cover tray adjacent to the ultraviolet lights are left untreated to allow for passage of UV radiation into the cavity defined by the base tray and cover tray, and the first and second long side walls of the cover tray, the cover tray top wall, the first and second short side walls of the base tray, the second long side wall of the base tray, and the base tray bottom wall are covered in the UV reflective material to enhance transmission of UV light to the surfaces of the product requiring sanitizing.

2. The storage and sanitizing case according to claim 1, further including a plurality of vertically oriented support posts upon which products may be secured.

3. The storage and sanitizing case according to claim 2, wherein each of the plurality of posts are made of quartz allowing for the passage of UV-C light therethrough.

* * * * *